US006310097B1

(12) United States Patent
Mitoma et al.

(10) Patent No.: US 6,310,097 B1
(45) Date of Patent: Oct. 30, 2001

(54) PROTECTING AND SURVIVAL PROMOTING AGENT FOR CENTRAL NERVOUS CELL

(75) Inventors: Jyunya Mitoma; Shigeki Furuya; Yoshio Hirabayashi, all of Saitama (JP)

(73) Assignees: Riken, Saitama; Taisho Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/463,393

(22) PCT Filed: Jul. 28, 1998

(86) PCT No.: PCT/JP98/03364

§ 371 Date: Apr. 17, 2000

§ 102(e) Date: Apr. 17, 2000

(87) PCT Pub. No.: WO99/04781

PCT Pub. Date: Feb. 4, 1999

(30) Foreign Application Priority Data

Jul. 28, 1997 (JP) .................................................... 9-201619

(51) Int. Cl.$^7$ ................................................. A61K 31/195

(52) U.S. Cl. ........................................................... 514/561

(58) Field of Search .................................................. 514/561

(56) References Cited

U.S. PATENT DOCUMENTS 5,728,728 * 3/1998 Kozachuk ............................. 514/483

OTHER PUBLICATIONS

Savoca et al., *J. Neurosci. Methods*, vol. 61, #1–2, pp. 159–167 (1995).
Wilcox et al., *J. Neurophysiol*, vol. 76, #5, pp. 3415–3424 (1996).
Mitoma et al., *Neurosci. Res.*, vol. 30, #2, pp. 195–199 (1998).
Wilcox et al, J. Neurophysiol, vol. 75, #5, pp. 3415–3424 (abstract), Nov. 1996.*
Savoca et al, J. Neurosci. Methods, vol. 61, #1–2, pp. 159–167 (abstract), Sep. 1995.*
Newell et al, Exp. Neurol., vol. 145, #1, pp. 235–244 (abstract), May 1997.*
Xu et al, J. Biol. Chem., vol. 266, #4, pp. 2143–2150 (abstract), Feb. 1991.*
Goslin et al., "Rat Hippocampal Neurons in Low–Density Culture", *Culturing Nerve Cells*, pp. 251–278.
Savoca et al., "Effects of L–serine on Neurons in Vitro", *Journal of Neuroscience Methods*, 61, pp. 159–167 (1995).
Enokido et al., "Apoptotic Cell Death Occurs in Hippocampal Neurons Cultured in a High Oxygen Atmosphere", *Neuroscience*, vol. 57, No. 4, pp. 965–972 (1993).

Kubo et al., "Brain–Derived Neurotrophic Factor (BDNF) Can Prevent Apoptosis of Rat Cerebellar Granule Neurons in Culture", *Developmental Brain Research*, 85, pp. 249–258 (1995).

Furuya et al., "Sphingolipid Biosynthesis is Necessary for Dendrite Growth and Survival of Cerebellar Purkinje Cells in Culture", *Journal of Neurochemistry*, vol. 65, No. 4, pp. 1551–1561 (1995).

Folch et al., "A Simple method for the Isolation and Purification of Total Lipides from Animal Tissues", *J. Biol. Chem*, 226, pp. 497–509 (1957).

Inoue et al., "Lecture of New Biochemical Experiments", *Shin Seikagaku Jikken Koza*, 4, pp. 37–47 (1991).

Taki et al., "A Simple and Quantitative Purification of Glycosphingolipids and Phospholipids by Thin–Layer Chromatography Blotting", *Analytical Biochemistry*, 223, pp. 232–238 (1994).

Kasama et al., "Microscale Analysis of Glycosphingolipids by TLC Blotting/Secondary Ion Mass Spectrometry: A Novel Blood Group A–active Glycosphingolipid and Changes in Glycosphingolipid Expression in Rat Mammary Tumour Cells with Different Metastatic Potentials", *Glycoconjugate Journal*, 13, pp. 461–469 (1996).

Kaibuchi et al., "Cooperative Roles of Various Membrane Phospholipids in the Activation of Calcium–activated, Phospholipid–dependent Protein Kinase", *The Journal of Biological Chemistry*, vol. 256, No. 14, pp. 7146–7149 (Jul. 25, 1981).

Furuya et al., "Ceramide and its Interconvertible Metabolite Sphingosine Function as Indispensable Lipid Factors Involved in Survival and Dendritic Differentiation of Cerebellar Purkinje Cells", *Journal of Neurochemistry*, vol. 71, No. 1, pp. 366–377 (1998).

* cited by examiner

*Primary Examiner*—James H. Reamer
(74) *Attorney, Agent, or Firm*—Greenblum & Bernstein P.L.C.

(57) ABSTRACT

An agent for enhancing cell survival of central nerve cells, which comprises a substance selected from the group consisting of L-serine, glycine, and fatty acid compounds thereof as an active ingredient, and a medicament for preventive and/or therapeutic treatment of cerebral dysfunction which comprises said substance as an active ingredient. The substance has an action for protecting cerebral cells to suppress cell death and prolong cell life. For example, cerebral cell death caused by cerebral edema or the raise of intracerebral temperature due to cerebral hemorrhage, cerebral infarction head injury and the like can be suppressed.

20 Claims, 4 Drawing Sheets

PROTECTING AND SURVIVAL PROMOTING AGENT FOR CENTRAL NERVOUS CELL

TECHNICAL FIELD

The present invention relates to an agent for protecting central nerve cells and enhancing survival thereof

BACKGROUND ART

Hippocampal neurons have widely been used in the field of the neurophysiology as central nerve cells that can be cultured in laboratories. It has been known that a significant number of the neurons die in one week from the start of the culture when the cells are primarily cultured alone. As a method for long-term culture of hippocampal neurons, co-culture of the cells with glial cells (gliacytes that fill spaces between neurons and their neurites) is known. However, since the culture system is not a monoculture system, it is not suitable for researches on auxotrophy of hippocampal neurons alone, neuronal responses to polypeptide neurotrophic factors and the like. As a method for culturing hippocampal neurons in the absence of glial cells, a method is known wherein the neurons are cultured in the presence of all non-essential amino acids. However, survival time of the cells and number of survived cells are significantly lower than those attained by the co-culture with glial cells.

In primary culture system of hippocampal neurons, it has also been known that long term survival of neurons can be achieved by the addition of culture supernatant of glial cells (astrocyte conditioned medium, ACM). A method for such culture has been established by Goslin et al. (Goslin, K. and Banker, G., "Culturing Nerve Cells", Ed. by Banker, G. et al., p.251–278, The MIP Press, England). However, it has not been revealed which substance in the culture supernatant enhances survival of the neurons.

It has also been known that L-serine acts as an important factor for morphodifferentiation of fowl ganglions which are peripheral nerve cells (Savoca, R., Ziegler, U. and Sonderegger, P., Journal of Neuroscience Methods, 61, pp.159–167, 1995). However, the action of L-serine disclosed in the publication is mainly focused on the morphogenesis of neurons, and the publication neither teaches nor suggests whether L-serine may have any action on the survival of neurons. Moreover, the cells used in the experimental system were peripheral nerve cells, which are totally different from central nerve cells such as hippocampal neurons in generation and functions. Therefore, action of L-serine on central nerve cells is not taught by the publication

DISCLOSURE OF THE INVENTION

An object of the present invention is to provide a substance that enhances survival of neurons. Another object of the present invention is to provide an agent for improving cerebral functions.

The inventors of the present invention eagerly conducted researches to achieve the foregoing objects. As a result, they found that glial cells secreted a cell survival-enhancing substance for hippocampal neurons, and the substance was not produced by the hippocampal neurons. They also found that the substance was L-serine. Moreover, the inventors of the present invention also found that L-serine or glycine had cell survival-enhancing action on central nerve cells such as cerebellar granule and Purkinje cells, as well as on hippocampal neurons. The present invention was achieved on the basis of these findings.

The present invention thus provides an agent for enhancing cell survival of central nerve cells, which comprises as an active ingredient a substance selected from the group consisting of L-serine, glycine, and fatty acid compounds thereof, preferably L-serine and/or glycine, more preferably L-serine. According to a preferred embodiment of the present invention, there is provided an agent for enhancing cell survival of central nerve cells which comprises L-serine as an active ingredient.

As another aspect of the present invention, there is provided a medicament for preventive and/or therapeutic treatment of cerebral dysfunction which comprises as an active ingredient a substance selected from the group consisting of L-serine, glycine, and fatty acid compounds thereof, preferably L-serine and/or glycine, more preferably L-serine. As other aspects of the present invention, there are provided use of a substance selected from the group consisting of L-serine, glycine, and fatty acid compounds thereof, preferably L-serine and/or glycine, more preferably L-serine, for manufacture of the aforementioned medicament for preventive and/or therapeutic treatment, and a method for preventive and/or therapeutic treatment of cerebral dysfunction which comprises the step of administering to a patient a preventively and/or therapeutically effective amount of a substance selected from the group consisting of L-serine, glycine, and fatty acid compounds thereof, preferably L-serine and/or glycine, more preferably L-serine.

As a further aspect of the present invention, there is provided a medium composition for culture of central nerve cells which contains L-serine or glycine as at agent for enhancing cell survival of central nerve cells.

BEST MODE FOR CARRYING OUT THE INVENTION

Figure 1:
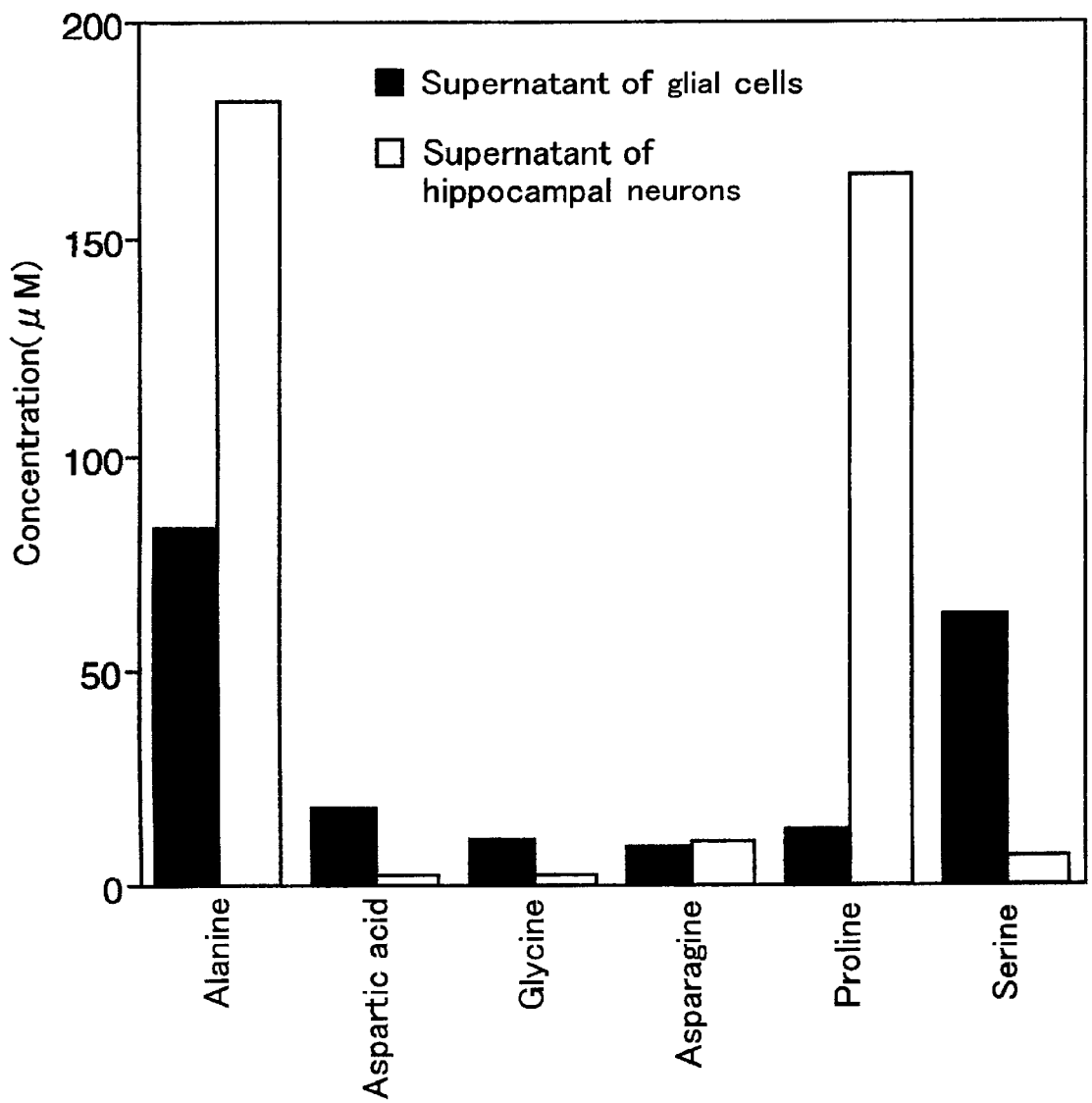
FIG. 1 depicts amino acid concentrations in culture supernatants of hippocampal glial cells and neurons.

The agent for enhancing cell survival according to the present invention is characterized to comprise, as an active ingredient, a substance selected from the group consisting of L-serine, glycine, and fatty acid compounds thereof, preferably L-serine and/or glycine, more preferably L-serine. As L-serine and glycine, an acid addition salt or a base addition salt thereof may be used. The fatty acid compounds of L-serine and glycine are not particularly limited, and for example, myristylated L-serine or glycine may preferably be used. The agent for enhancing cell survival according to the present invention has an action of suppressing cell death of central nerve cells such as hippocampal neurons, cerebellar granule and Purkinje cells to protect these cells, and an action of enabling long-time survival of these cells. Cells to be applied by the agent for enhancing cell survival of the present invention are not particularly limited, and the agent can be applied to any central nerve cells.

The agent for enhancing cell survival of the present invention can be used for culture of central nerve cells by the addition to a culture medium. Coexistence of glial cells is not required in the culture system, and accordingly, central nerve cells can be cultured for a long period of time as a single-cell system. An example of a medium composition for the culture of central nerve cells provided by the present invention includes a medium composition consisting of Eagle's MEM (25 mM of HEPES, 30 nM of sodium selenite, 500 $\mu$M of sodium pyruvate, 3.9 mM of glutamine, 16.7 mM of glucose, 100 $\mu$M of putrescine, 10 $\mu$g/ml of gentamycin sulfate and 0.1 mg/ml of bovine serum albumin as final concentrations) supplemented with about 10 to 200 $\mu$M, preferably about 50 to 100 $\mu$M of L-serine or glycine, preferably L-serine. However, the medium compositions of the present invention are not limited to the aforementioned medium, and it should be understood that any medium compositions fall within the scope of the present invention in which L-serine or glycine, preferably L-serine, is added as an agent for enhancing cell survival, for example at a concentration as mentioned above, to an appropriate medium available to those skilled in the art.

The agent for enhancing cell survival provided by the present invention can be used as an active ingredient of a medicament for preventive and/or therapeutic treatment of cerebral dysfunction. The medicament of the present invention has an action of protecting cerebral cells to suppress cell death and prolonging cell life. Therefore, the medicament of the present invention can prevent cerebral dysfunction, and/or improve cerebral dysfunction caused by reduction of the survivability of cerebral cells. Diseases to be applied by the medicament of the present invention are not particularly limited, and the medicament can be used for preventive and/or therapeutic treatment of various diseases with cerebral dysfunction. For example, the medicament can suppress cerebral cell death caused by cerebral edema or the raise of intracerebral temperature due to cerebral hemorrhage, cerebral infarction, head injury and the like. The medicament can also prevent onset of senile dementia by suppressing reduction of number of cerebral cells due to aging. Furthermore, the medicament is also useful for preventive and/or therapeutic treatment of diseases resulting from degeneration of cerebral cells such as, for example, Alzheimer's disease, Parkinson's disease, Huntington's chorea and the like.

As the medicament of the present invention, one or more of substances selected from the group consisting of L-serine, glycine, and fatty acid compounds thereof can be used. As the medicament of the present invention, physiologically acceptable salts of said substances may be used, and hydrates and solvates of the substances in a free form or physiologically acceptable salts thereof may also be used.

The aforementioned substances, per se, may be used as the medicament of the present invention. However, it is generally preferred to prepare and use a pharmaceutical composition comprising the aforementioned substance as an active ingredient by using pharmacologically and pharmaceutically acceptable additives available to those skilled in the art. As the pharmacologically and pharmaceutically acceptable additives, for example, excipients, disintegrators or disintegrating aids, binders, lubricants, coating agents, colorants, diluents, base materials, dissolving agents or dissolving aids, isotonic agents, pH modifiers, stabilizers, propellants, adhesives and the like may be used. Examples of formulations suitable for oral administration include, for example, tablets, capsules, subtilized granules, granules, solutions, syrups and the like. Examples of formulations suitable for parenteral administration include, for example, injections, drip infusions, suppositories, inhalants, transmucosal preparations, transdermal preparations, nasal drops, ear drops, patches and the like.

For formulations suitable for oral, transdermal or transmucosal administration, excipients such as glucose; disintegrators or disintegrating aids such as carboxymethylcellulose; binders such as hydroxymethylcellulose; lubricants such as magnesium stearate; coating agents such as hydroxypropylmethylcellulose; bases such as Vaseline petroleum jelly and the like may be used as the pharmacologically and pharmaceutically acceptable additives. As the pharmacologically and pharmaceutically acceptable additives, propellants such as compressed gases; tackifiers such as sodium polyacrylate; base fabrics such as cotton cloth and so forth may also be used. For formulations suitable for injection or drip infusion, aqueous mediums such as distilled water for injection; dissolving agents or dissolving aids which can constitute injections that are dissolved upon use; isotonic agents such as glucose; pH modifiers such as inorganic acids, organic acids, inorganic bases and organic bases and the like may be used.

Doses of the medicament of the present invention may vary depending on various factors including a type of a disease, conditions and age of a patient, purpose of preventive or therapeutic treatment and the like, and the dose may suitably be determined by those skilled in the art in view of these factors. The inventors of the present invention revealed that about 10 to 200 $\mu$M, preferably about 50 to 100 $\mu$M of L-serine or glycine, preferably L-serine, was required for optimal survival of central nerve cells. It is thus suggested that this level of L-serine is supplied by glial cells under a physiological condition in living bodies. Therefore, in order to suppress cell death of cerebral cells, it is desirable to appropriately chose doses so that cerebral cells can contact with L-serine or glycine, preferably L-serine, at the above concentration. The agent for preventive and/or therapeutic treatment of cerebral dysfunction of the present invention may be used as food additives, and may be used as an ingredient of health food or drinks.

EXAMPLES

The present invention will be more specifically explained with reference to the following examples. However, the scope of the present invention is not limited to these examples.

(1) Materials and Methods
(a) Materials

Wistar/ST rats at the 18th day of definite pregnancy were purchased from Japan SLC Co., Ltd. Eagle's MEM and bovine fetal serum were purchased from Gibco, and culture plates were from Sumitomo Bakelite Co., Ltd. and Becton Dickinson. All of the amino acids used were L-amino acids.

(b) Primary Culture of Rat Hippocampal Neurons and Glial Cells

The primary culture of rat hippocampal neurons was performed according to a method previously reported (Enokido Y., and Hatanaka, H., Neuroscience, 57, pp.965–972, 1993). As the medium, Eagle's MEM was used (containing 25 mM of HEPES, 30 nM of sodium selenite, 500 $\mu$M of sodium pyruvate, 3.9 mM of glutamine, 16.7 mM of glucose, 100 $\mu$M of putrescine, 10 $\mu$g/ml of gentamycin sulfate and 0.1 mg/ml of bovine serum albumin as final concentrations). The culture plates used were those coated with polyethyleneimine beforehand.

For counting of cell number and morphological observation of cells, $2 \times 10^5$ cells were suspended in 200 $\mu$l of the medium containing 10% beat-inactivated bovine fetal serum and plated in each of 35 mm diameter wells of 6-well plates. For lipid extraction, $2 \times 10^6$ cells were suspended in 2 ml of the culture medium and plated on a culture plate of 100 mm in diameter. The cells were incubated in a 5% $CO_2$ incubator for 2 hours, then the medium was changed to 1 ml (for 35 mm well) or 6 ml (for 100 mm plate) of a serum free medium (containing 10 $\mu$g/ml of insulin, 100 $\mu$g/ml of apotransferrin and 20 nM progesteron instead of the heat-inactivated bovine fetal serum) supplemented with additives including non-essential amino acids, and the culture was further continued overnight. On the next day, the medium was changed to the serum free medium containing 1 $\mu$M of cytosine arabinoside to inhibit the proliferation of glial cells, and the culture was continued.

Glia cells, dispersed in the same manner as described above, were suspended in Eagle's MEM containing 10% of heat-inactivated bovine fetal serum and plated on an uncoated plate, and then cultured until they became confluent. Then, the cells were dispersed with trypsin-EDTA, and subcultured in the same medium once or twice. When the cells became confluent again, the medium was changed to the above-mentioned serum free medium.

(c) Primary Culture of Cerebellar Neurons

Primary cultures of cerebellar granule and Purkinje cells were performed according to the method of Kubo et al. (Kubo T., Nonomura T., Enokido, Y, and Hatanaka, H., Dev. Brain Res., 85. pp.249–258, 1995) and the method of Furuya et al. (Furuya S., Ono, K., and Hirabayashi, Y., J. Neurochem., 65, pp.1551–1561, 1995), respectively.

(d) Immunostaining

Stainings of neurons with anti-MAP2 (Microtubule-associated protein 2) monoclonal antibodies (Boebringer Mannheim) and anti-calbindin monoclonal antibodies (Sigma) were performed according to the method of Enokido et al. (Enokido, Y., and Hatanaka, H., Neuroscience, 57, pp.965–972, 1993) and the method of Furuya et al. (Furuya, S., Ono, K., and Hirabayashi, Y., J. Neurochem., 65, pp.1551–1561, 1995), respectively.

(e) Lipid Analysis

Cultured cells were harvested, and total lipids were extracted with chloroform/methanol (½, volume ratio). The extract was subjected to partition into two layers by the partition method of Folch (Folch, J., Lees, M., and Sloane-Stanley, G. H., J. Biol. Chem., 226, pp.497–509, 1957). Then, thin layer chromatography was carried out by using an HPTLC plate (Silica Gel 60 HPTLC plate, Merck). As a developing solvent, chloroformlmethanol/formic acid/acetic acid/1 M magnesium chloride (60/30/6.5/4.5/0.1, volume ratio) was used for the development of phospholipids (chloroform layer), and chloroformlmethanol/12 mM magnesium chloride (5/4/1, volume ratio) was used for the development of glycolipids (aqueous layer). The bands were detected with the primulin reagent (non-specific), iodine vapor (non-specific), ninhydrin (amino group), and the Ryu-MacCoss's reagent (phosphate group) (Inoue, K., Nagai, K., and Sekiyama, Y., Lecture of New Biochemical Experiments (Shin Seikagaku Jikken Koza), 4, pp.37–47, 1991).

(f) Amino Acid Analysis and Mass Spectrometry

As for the amino acids in the culture supernatants, each solution was treated with 5% trichloroacetic acid or 5% perchloric acid and centrifuged, and then the supernatant was used as a sample for amino acid analysis. As for the amino acids in lipids, the lipids were developed by thin layer chromatography and then extracted, and then hydrolyzed with 6 N hydrochloric acid to obtain samples for amino acid analysis. The amino acid analysis was performed by using an amino acid analyzer, Hitachi S-8500A. The purification of the lipids by TLC blotting and the mass spectrometry (SIMS analysis) were performed by methods previously reported (Taki T., Kasama, T., Handa, S., and Ishikawa, D., Anal. Biochem., 223, pp.232–238, 1994; Kasama, T., Hisano, Y., Nakajima, M, Handa, S., and Taki, T., Glycoconj. J., 13, pp.461–469, 1996). The quantification of proteins was performed by using a BCA protein measurement kit of Pierce and bovine serum albumin as a standard.

(2) Results (a) The Eagle's MEM (minimum essential medium) does not contain non-essential amino acids (alanine, aspartic acid, glutamic acid, glycine, asparagine, proline, serine), and hippocampal neurons cannot be cultured for a long period of time in the medium. The fact suggests that these non-essential amino acids are possibly supplied from glial cells which coexist with the neurons in living bodies. First, studies were focused on what kinds of amino acids were secreted from neurons and glial cells. Neurons and glial cells of rat hippocampus were separately cultured in serum free Eagle's MEM, and then culture supernatants were collected after one week and non-essential amino acid concentrations in acid-soluble fractions of the supernatants were determined. As a result, it was found that serine, glycine and aspartic acid were present at higher concentrations compared to the other amino acids in the culture supernatant of the glial cells (Astrocyte conditioned medium, ACM) (FIG. 1).

Figure 2:
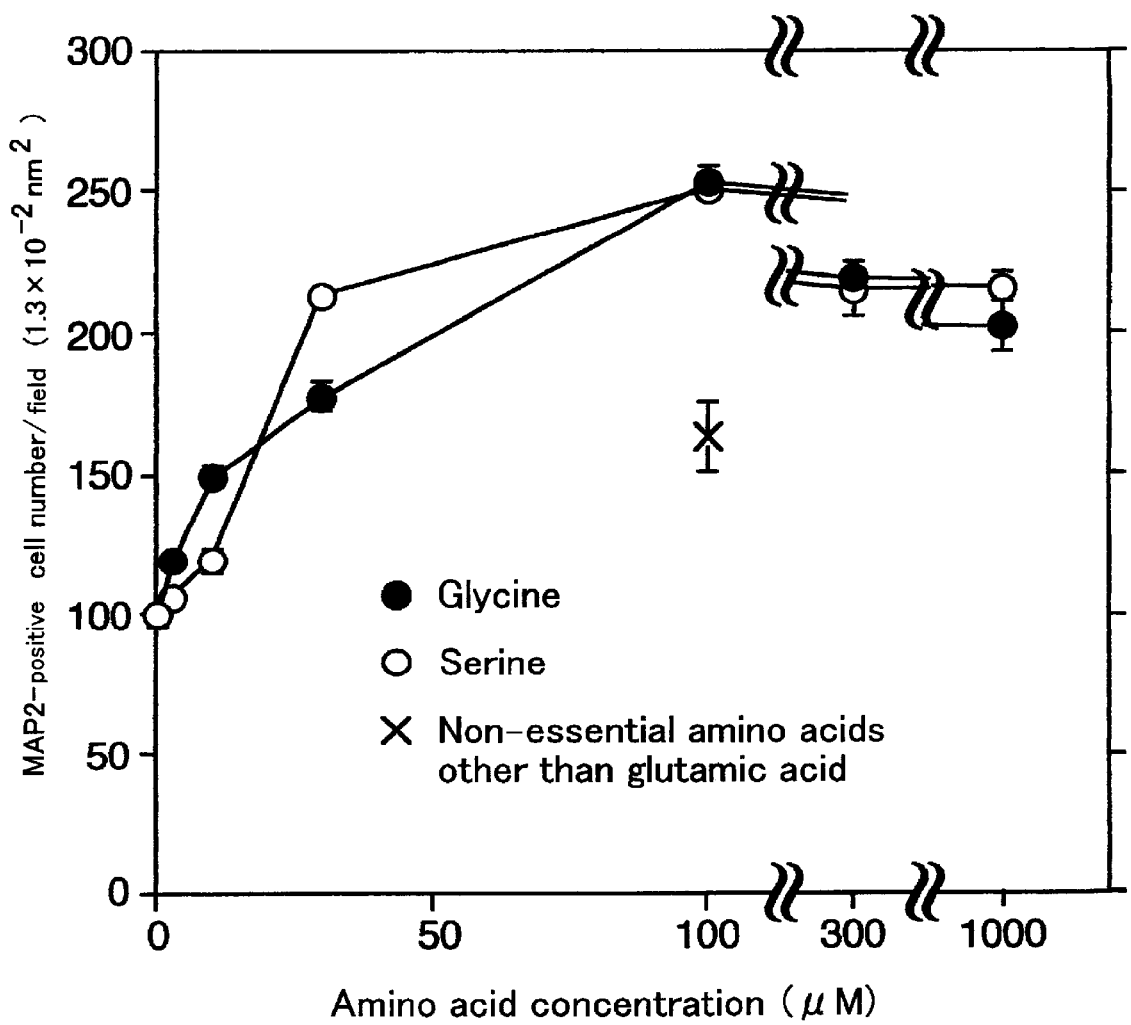
FIG. 2 depicts effects of non-essential amino acid concentrations on survival of hippocampal neurons.

Hippocampal neurons were cultured for six days in the presence or absence of various non-essential amino acids, and then morphology of the neurons was examined by staining the cells with anti-MAP2 antibodies. As a result, elongation of dendrites and improvement of survival rate were observed when serine and glycine were added. No survival-enhancing activity was observed in aspartic acid, asparagine, proline, alanine, and glutamic acid. In order to investigate the effect of non-essential amino acid concentrations on survival of hippocampal neurons, hippocampal neurons were cultured for six days in the presence of various non-essential amino acids, and the cells were stained with anti-MAP2 antibodies and then the cell number was counted. The results are shown in FIG. 2. Means of the results obtained by 3 experiments ± standard errors are indicated in the graph. Both serine and glycine gave the highest survival-enhancing activity at a concentration of about 50 to 100 $\mu$M.

Figure 3:
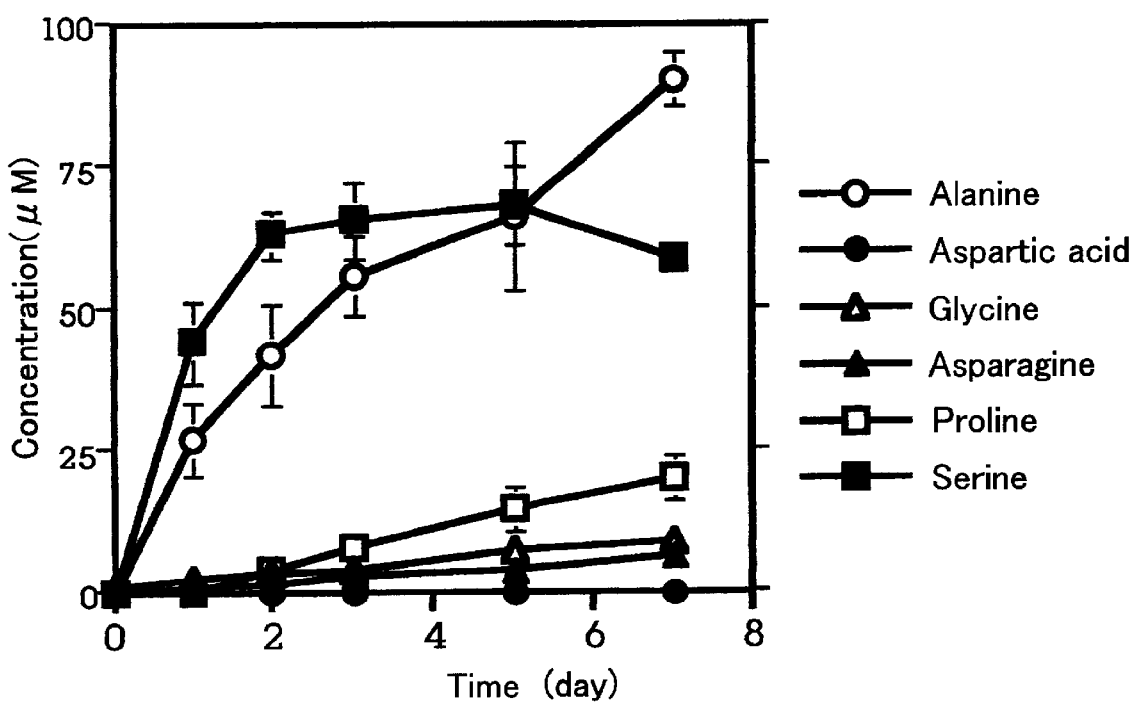
FIG. 3 depicts changes with time of non-essential amino acid concentrations in culture supernatant of glial cells.

Culture supernatants of the glial cells were collected with time and non-essential amino acid concentrations of acid-soluble fractions were determined to study changes with time of non-essential amino acid concentrations in the culture supernatant of the glial cells. The results are shown in FIG. 3. Means of the results obtained by 3 experiments ± standard errors are indicated in the graph. It was found that serine was more rapidly secreted extracellularly than the other amino acids, and reached to an equilibrium at a concentration of about 70 $\mu$M after culture for two days. Since this concentration can maintain the survival of neurons, the phenomenon was considered to be physiologically significant. On the other hand, glycine was not secreted at a concentration required for the maintenance of neuronal survival. From the above results, it was concluded that serine was essential for the survival of hippocampal neurons, and its necessary amount was secreted from glial cells.

(b) The above results suggest a possibility that serine transmits a signal to neurons for enhancing survival of the neurons, or that serine cannot be synthesized in neurons to allow depletion. The former possibility was denied because no variation in phosphorylation of proteins was observed before and after the addition of serine Accordingly, to verify the possibility that serine cannot be synthesized in neurons to allow depletion, serine-containing lipids present in cytoplasmic membranes of neurons were examined.

Hippocampal neurons were cultured for six days in the presence or absence of 100 $\mu$M of serine or glycine, and lipids were extracted and subject to the Folch partition. The chloroform layer and the aqueous layer were developed by TLC, and colored with ninhydrin and the primulin reagent, respectively, to detect lipids. As a result, the amount of phosphatidylserine was found to be relatively low among the lipid components of the chloroform layer in the cells cultured in the absence of serine, and formation of a new lipid component (X-3) was observed at a position slightly above phosphatidylserine. In a fraction of the aqueous layer, GT1b ganglioside or unidentified lipids, observed in the presence of serine, disappeared in the absence of serine.

The structure of the lipid (X-3) emerged in the absence of serine was analyzed. The lipid was positive both for the Ryu-MacCoss reaction and the ninhydrin reaction, suggesting that the lipid was an amino group-containing phospholipid. The band of the lipid (X-3) on the TLC plate was detected with iodine vapor, purified and hydrolyzed, and then subjected to amino acid analysis using a portion of the TLC plate as a control which was not stained with iodine. As a result, presence of threonine was detected. The lipid (X-3) was purified by the TLC-blotting method and subjected to the SIMS analysis. The lipid was detected as two peaks of fatty acids having different lengths with two sodium atoms (846, 18:1/18:0 and 870, 20:3/18:0). Accordingly, the lipid was identified as phosphatidylthreonine.

The above results indicate that, when serine is not supplied, threonine is utilized as an alternate and phosphatidylthreonine is biosynthesized. Therefore, it is considered that neurons themselves do not have an ability to synthesize serine, and the supply of serine required for the synthesis of phosphatidylserine mainly depends on glial cells. Phosphatidylserine is an essential lipid for the activation of protein kinase C, which is indispensable to survival of neurons (Kaibuchi K., Takai, Y., and Nishizuka, Y., J. Biol. Chem., 256, pp.7146–7149, 1981). Depletion of the lipid is considered to be one of factors threatening the survival of the cells. There has been no report as far the presence of phosphatidylthreonine in the nerve.

Serine is usually biosynthesized from glucose through 3-phosphoglycerate, which is an intermediate metabolite of the glycolysis system, by the 3-step enzymatic reaction, i.e., 3-phosphoglyceric acid→(phosphoglyceric acid dehydrogenase)→3-phosphohydroxypyruvic acid→(phosphoserine transaminase)→phosphoserine→(phosphoserine phosphatase)→serine. The above results revealed that glial cells rapidly secrete serine that is biosynthesized by the pathway, whist the synthesis of serine is very reduced in hippocampal neurons for some reasons, and the cells seems to be dependent on the supply from glial cells.

Glycine also suppressed the cell death of neurons. This phenomenon can be interpreted that serine is easily synthesized from glycine by serine hydroxymethyltransferase after incorporation into the cells. However, because serine is also used as a precursor for the de novo synthesis of glycine, which is catalyzed by serine hydroxymethyltransferase, depletion of serine also leads to depletion of glycine. Therefore, it is considered that protein syntheses are inevitably affected by the lack of these two amino acids.

(c) The survival-enhancing effect of serine was observed in cerebellar granule cells, as well as in hippocampal neurons.

When culture of cerebellar granule cells was continued after the whole medium was changed to serum free medium not containing serine on the 7th day from the start of the culture, most of the cells caused cell death on the 7th day from the medium change. In contrast, when the cells were cultured after the whole medium was changed to the medium added with 200 $\mu$M of serine, the cell death was completely suppressed and the morphology of the cells was maintained. Similarly, serine was also found to have survival-enhancing effect in cerebellar Purkinje cells. Therefore, it can be concluded that serine synthesis is generally insufficient for cell survival in central nerve cells.

Figure 4:
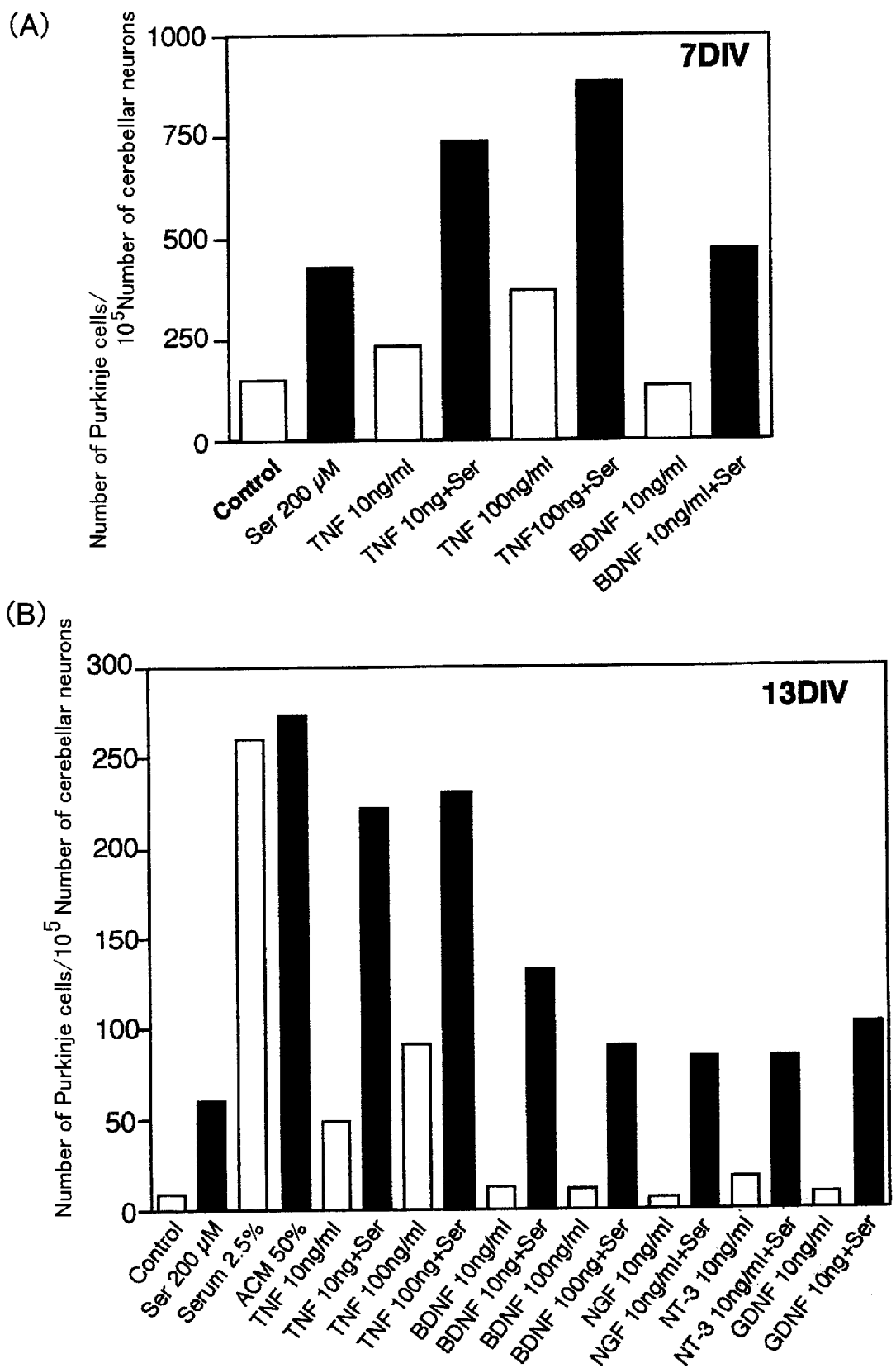
FIG. 4 depicts effect of serine on primary culture of cerebellar Purkinje cells. White bars show results obtained in the absence of serine, and black bars in the presence of 200 $\mu$M of serine. The abbreviations are as follows: Ser: L-serine; TNF: tumor necrosis factor-$\alpha$; BDNF: brain-derived neurotrophic factor; NT-3: neurotrophin-3; NGF: nerve growth factor; and GDNF: glial cell line-derived neurotrophic factor.

In order to confirm the effect of serine on primary culture of cerebellar Purkinje cells, cerebellar Purkinje cells were subjected to several treatments shown in FIG. 4, and cultured for six days (A) or 12 days (B). Then, the Purkinje cells were stained with anti-calvindin antibodies, and cell number was counted The results are shown in FIG. 4. In the figure, the white bars represent results obtained in the absence of serine, and the black bars represents results obtained in the presence of 200 $\mu$M of serine. Serine was revealed to have an activity for enhancing the activities of tumor necrosis factor-$\alpha$(TNF-$\alpha$), and proteinaceous nutritional factors such as brain-derived nerotrofic factor (BDNF).

Industrial Applicability

The medicament of the present invention has an action for protecting central nerve cells to suppress cell death and prolong cell life. Therefore, the medicament of the present invention can prevent cerebral dysfunction, and/or improve cerebral dysfunction caused by reduction of cerebral cell survivability.

What is claimed is:

1. A method for preventive and/or therapeutic treatment of cerebral dysfunction, comprising:
   administering to a patient in need of such treatment a preventively and/or therapeutically effective amount of a composition comprising at least one of L-serine, glycine, fatty acid compounds thereof, physiologically acceptable salts thereof, hydrates thereof, and solvates thereof.

2. The method of claim 1, wherein the composition further comprises an additive comprising at least one of an excipient, disintegrator, disintegrating aid, binder, lubricant, coating agent, colorant, diluent, base material, dissolving agent, isotonic agent, pH modifier, stabilizer, propellant, and adhesive.

3. The method of claim 2, wherein the additive comprises an excipient comprising glucose.

4. The method of claim 2, wherein the additive comprises a disintegrator or disintegrating aid comprising carboxymethylcellulose.

5. The method of claim 2, wherein the additive comprises a binder comprising hydroxymethylcellulose.

6. The method of claim 2, wherein the additive comprises a lubricant comprising magnesium stearate.

7. The method of claim 2, wherein the additive comprises a coating agent comprising hydroxypropylmethylcellulose.

8. The method of claim 2, wherein the additive comprises petroleum jelly.

9. The method of claim 2, wherein the additive comprises a propellant comprising compressed gas.

10. The method of claim 2, wherein the additive comprises sodium polyacrylate.

11. The method of claim 2, wherein the additive comprises cotton cloth.

12. The method of claim 2, wherein the additive comprises distilled water.

13. The method of claim 2, wherein the additive comprises an isotonic agent comprising glucose.

14. The method of claim 2, wherein the additive comprises a pH modifier comprising at least one of inorganic acid, organic acid, inorganic base, and organic base.

15. The method of claim 1, wherein the composition comprises one of a tablet, capsule, subtilized granule, granule, solution, syrup, health food, and health drink.

16. A method for enhancing central nerve cell survival, comprising:

intravenously administering by drip infusion in an amount effective for enhancing central nerve cell survival, of a composition to a patient in need of such treatment, wherein the composition comprises at least one of L-serine, glycine, fatty acid compounds thereof, physiologically acceptable salts thereof, hydrates thereof, and solvates thereof.

17. The method of claim 16, wherein the composition further comprises an additive comprising at least one of a dissolving agent, isotonic agent, and pH modifier.

18. The method of claim 17, wherein the additive comprises an isotonic agent comprising glucose.

19. The method of claim 17, wherein the additive comprises a pH modifier comprising at least one of inorganic acid, organic acid, inorganic base, and organic base.

20. A method for enhancing central nerve cell survival, comprising:

ingesting an effective amount of a health drink comprising at least one of L-serine, glycine, fatty acid compounds thereof, physiologically acceptable salts thereof, hydrates thereof, and solvates thereof.

* * * * *

UNITED STATES PATENT AND TRADEMARK OFFICE
CERTIFICATE OF CORRECTION

PATENT NO.   : 6,310,097 B1
DATED        : October 30, 2001
INVENTOR(S)  : J. Mitoma et al.

It is certified that error appears in the above-identified patent and that said Letters Patent is hereby corrected as shown below:

Title page,
Item [56], References Cited, the following FOREIGN PATENT DOCUMENTS were omitted and should be included:
-- 452299        10/16/91        EPO
4-91034          03/24/92        JAPAN --
Item [57], ABSTRACT,
Line 12, after "infarction" insert -- , --.

Signed and Sealed this

Seventeenth Day of September, 2002

Attest:

JAMES E. ROGAN
Attesting Officer      Director of the United States Patent and Trademark Office